United States Patent [19]

Faupel

[11] Patent Number: 5,099,844
[45] Date of Patent: Mar. 31, 1992

[54] DISCRIMINANT FUNCTION ANALYSIS METHOD AND APPARATUS FOR DISEASE DIAGNOSIS AND SCREENING

[75] Inventor: Mark L. Faupel, Conyers, Ga.
[73] Assignee: Biofield Corp., New York, N.Y.
[21] Appl. No.: 579,970
[22] Filed: Sep. 10, 1990

Related U.S. Application Data

[62] Division of Ser. No. 288,572, Dec. 22, 1988, Pat. No. 4,955,383.

[51] Int. Cl.⁵ ............................................. A61B 5/05
[52] U.S. Cl. ................................ 128/653.1; 128/734; 128/639
[58] Field of Search ............... 128/733, 734, 736, 630, 128/639, 653 R, 653.1

[56] References Cited

U.S. PATENT DOCUMENTS

| | | | |
|---|---|---|---|
| 4,078,553 | 3/1978 | Duroux ............................. | 128/734 |
| 4,291,708 | 9/1981 | Frei et al. | |
| 4,328,809 | 5/1982 | Hirschowitz et al. .......... | 128/653 R |
| 4,557,271 | 12/1985 | Stoller et al. ................... | 128/639 |
| 4,674,518 | 6/1987 | Salo ................................... | 128/734 |
| 4,794,934 | 1/1989 | Motoyama et al. .............. | 128/734 |

FOREIGN PATENT DOCUMENTS 0050353  4/1982  European Pat. Off. .

Primary Examiner—Lee S. Cohen
Assistant Examiner—Krista M. Pfaffle
Attorney, Agent, or Firm—Sixbey, Friedman, Leedom & Ferguson

[57] ABSTRACT

A method and apparatus for determining the presence or absence of a disease condition at a test site on a human or animal subject by detecting during a test period the respective electrical potentials of the electromagnetic field present in the subject between each of a plurality of measurement locations in the area of the test site and at least one reference location. A representative potential is separately obtained for each measurement location during the test period, and these representative potentials are compared at the end of the test period to obtain relationships therebetween which are indicative of either the presence or absence of a disease condition.

18 Claims, 5 Drawing Sheets

DISCRIMINANT FUNCTION ANALYSIS METHOD AND APPARATUS FOR DISEASE DIAGNOSIS AND SCREENING

This is a divisional application of Ser. No. 07/288,572, now U.S. Pat. No. 4,955,383, filed Dec. 22, 1988.

TECHNICAL FIELD

The present invention relates generally to a method and apparatus for diagnosing or screening disease states in a living organism by detecting the potential of the electromagnetic field present between a reference and a plurality of test points on the living organism to measure the gradient of electrical activity which occurs as a function of underlying biological activity.

BACKGROUND ART

In recent years the theory that measurement of the potential level of the electromagnetic field of a living organism can be used as an accurate diagnostic tool is gaining greater acceptance. Many methods and devices have been developed in an attempt to implement this theory. For example, U.S. Pat. No. 4,328,809 to B.H. Hirschowitz et al deals with a device and method for detecting the potential level of the electromagnetic field present between a reference point and a test point of a living organism. Here, a reference electrode provides a first signal indicative of the potential level of the electromagnetic field at the reference point, while a test electrode provides a second signal indicative of the potential level of the electromagnetic field at the test point. These signals are provided to an analog-to-digital converter which generates a digital signal as a function of the potential difference between the two, and a processor provides an output signal indicative of a parameter or parameters of the living organism as a function of this digital signal.

Similar biopotential measuring devices are shown by U.S. Pat. No. 4,407,300 to Davis, and U.S. Pat. No. 4,557,271 and 4,557,273 to Stoller et al. Davis in particular discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al patent contemplates the use of a plurality of test electrodes, while U.S. Pat. No. 4,416,288 to Freeman and U.S. Pat. No. 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and the devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated on or near the disease site to provide a measurement of the polarity of the signal received from the site relative to that from the reference site. Where multiple measuring electrodes have been used, their outputs have merely been summed and averaged to obtain one average signal from which a polarity determination is made. This approach is subject to major deficiencies which lead to diagnostic inaccuracy.

First, the polarity of diseased tissue underlying a recording electrode has been found to change over time. This fact results in a potential change which confounds reliable diagnosis when only one recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These effects alter ionic concentrations which can be measured at the skin surface. Other local effects, such as distortions in biologically closed electrical circuits, may also occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). Once this fact is recognized, it follows that important electrical indications of disease are going to be seen in the relative voltages recorded from a number of sites at and near a diseased area, and not, as previously assumed, on the direction (positive vs. negative) of polarity.

DISCLOSURE OF THE INVENTION

It is a primary object of the present invention to provide a novel and improved method and apparatus for providing a discriminant function analysis for disease diagnosis. Such method and apparatus operate to determine the relationships between a set of voltages taken from the area of a disease site on a living organism.

Another object of the present invention is to provide a novel and improved method and apparatus for the discriminant analysis of a disease site on a living organism wherein voltage potentials are measured in the area of the disease site over time. A maximum voltage differential is obtained from an average of multiple readings taken over time which constitutes a minimum voltage that is subtracted from a maximum voltage where two or more electrodes are recording voltages simultaneously or concurrently from a specific disease site or organ.

A further object of the present invention is to provide a novel and improved method and apparatus for providing a discriminant analysis for cancer diagnosis. Relative voltages are recorded from a number of sites at and near a diseased area using a variety of different electrode arrays depending on the intended application. A discriminant analysis is then used to determine the relationships between a set of voltages taken from such sites, and subsets of voltage relationships are used to provide a diagnosis of either the presence or absence of serious disease.

Yet another object of the present invention is to provide a novel and improved method and apparatus for providing a discriminant function analysis for screening a site on a living organism for a disease condition. Potential levels are taken from a plurality of locations at the site being screened, and the potential levels obtained are analyzed mathmatically to produce greater accuracy. Thus the relationships between the potentials obtained and different subsets of such relationships are analyzed to indicate either the presence or absence of a disease condition.

A still further object of the present invention is to provide a novel and improved method and apparatus for discriminant analysis in cancer diagnosis. Recordings from multiple sites at or near a disease site are taken and the voltage levels recorded from multiple sites are analyzed in terms of a discriminant mathematical analysis to produce greater diagnostic accuracy. Different electrode arrays, electrode shapes and electrode patterns are employed depending upon the intended application, and for some diagnostic procedures, the electrode array covers various areas of a lesion as well as relatively normal tissue near the lesion site. The aim of the method and apparatus is to measure the gradient of electrical activity which occurs as a function of the underlying biological activity of a specific organ system. Relationships between a set of voltages taken simultaneously or concurrently from a lesion site and possibly adjacent areas are derived, and different subsets of such relationships are obtained to indicate either the presence or absence of serious disease. The method and apparatus may be effectively employed in screening procedures to determine if a disease condition is likely to be present.

BEST MODE FOR CARRYING OUT THE INVENTION

Figure 1:
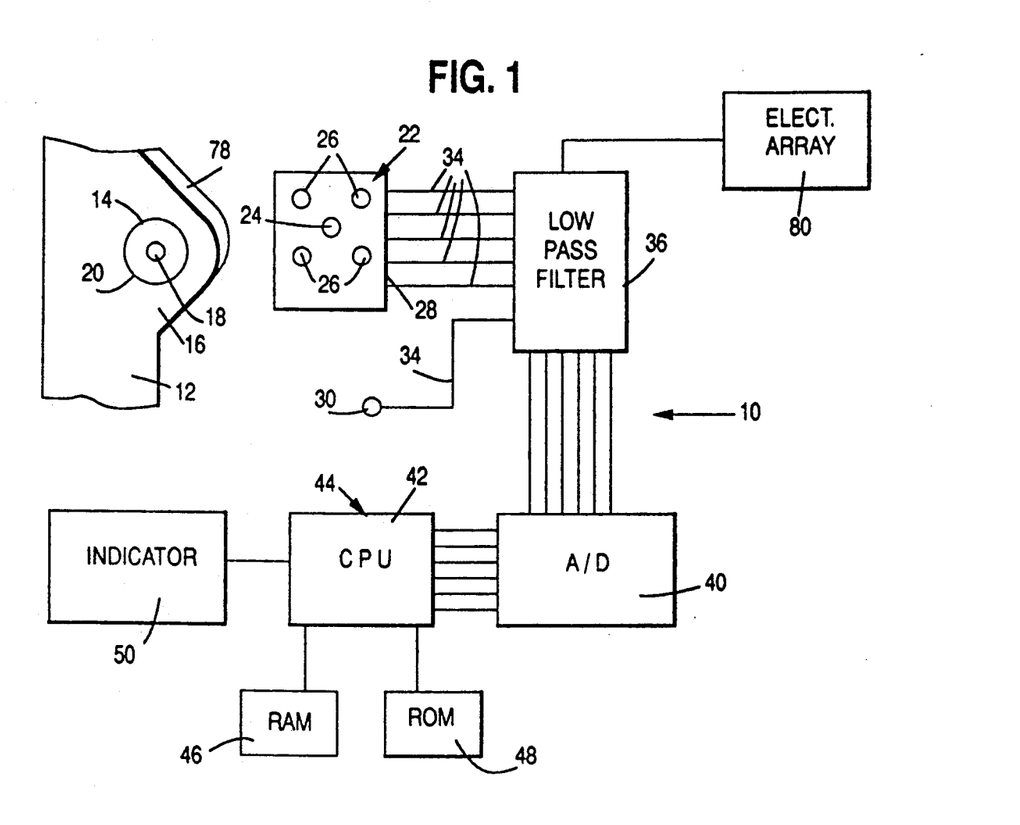
FIG. 1 is a block diagram of the apparatus of the present invention.

FIG. 1 discloses a basic block diagram of the apparatus of the present invention indicated generally at 10 for performing a discriminant analysis for disease screening or diagnosis. For purposes of illustration, the apparatus 10 will be described in connection with methods involving the screening for, or diagnosing of breast cancer. However, it should be recognized that the method and apparatus of the invention can be similarly employed for screening or diagnosis at other disease sites involving other portions or organs of a living human or animal.

In FIG. 1, a human subject 12 may have a cancerous lesion 14 on one breast 16. This cancerous lesion has a core 18 and an outer zone 20 surrounding the core where various differing local effects, such as changes in vascularization, water content and cell division rate occur. Assuming first, for purposes of discussion, that the location of the lesion 14 is not known, and the device 10 is to be used to screen the breast 16 to determine whether or not a disease condition exists, skin surface potentials will be measured in an area of the breast, including the zone 20 using an electrode array 22. In FIG. 1, the electrode array includes a central electrode 24 surrounded by four peripheral electrodes 26. However, the device and method of this invention contemplate the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. For breast cancer screening (where patients are asymptomatic) the array should give maximum coverage of the entire breast surface. The aim in both of these cases is to measure the gradient of electrical activity which occurs as a function of the underlying biological activity of the organ system. The number of electrodes used in the measurement will also be a function of specific application, and breast cancer screening may require the use of as few as twelve or as many as forty or more electrodes for each breast, while in screening for prostate cancer, as few as two measurement electrodes might be used.

Figure 2:
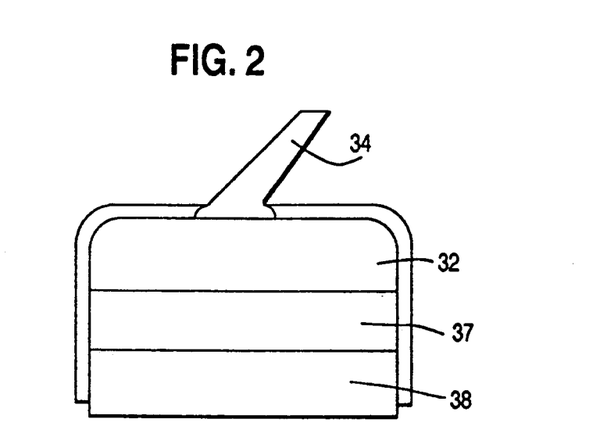
FIG. 2 is a sectional diagram of an electrode for the apparatus of FIG. 1.

The core electrode 24 and the peripheral electrodes 26 are mounted upon a flexible backing sheet 28 which permits the electrodes to be positioned against the curved surface of the breast 16 while still maintaining the position of the electrodes in a predetermined pattern. However, other electrode arrays may be employed wherein each individual electrode can be individually positioned, and the relative position between electrodes can be altered. The electrode array 22 is used in conjunction with a reference electrode 30, and all of these electrodes may be of a known type used for detecting the potential level of the electromagnetic field present in a living organism. Ideally, the electrodes 24, 26 and 30 should be of a type which do not cause a substantial battery effect between the organism under test and the electrode. A common electrode suitable for use as the electrodes 24, 26 and 30 is illustrated in FIG. 2, and includes a layer of silver 32 having an electrical lead 34 secured in electrical contact therewith. In contact with the silver layer 32 is a layer 37 of silver chloride, and extending in contact with the silver chloride layer is a layer of bridging material 38, such as sodium chloride, which contacts the surface of a living organism.

The device 10 is a multi-channel device having electrode leads 34 extending separately from the central electrode 24, the peripheral electrodes 26, and the reference electrode 30 to a low pass filter 36. This filter operates to remove undesirable high frequency AC components which appear on the slowly varying DC voltage signal outputs provided by each of the electrodes as a result of the electromagnetic field measurement. The low pass filter 36 may constitute one or more multiple input low pass filters of known type which separately filter the signals on each of the input leads 34 and then pass each of these filtered signals in a separate channel to a multiple input analog-to-digital converter 40. Obviously, the low pass filter 36 could constitute an individual low pass filter for each of the specific channels represented by the leads 34 which would provide a filtering action for only that channel, and then each filtered output signal would be connected to the input of the analog-to-digital converter 40.

The converter 40 is a multiple input multiplex analog-to-digital converter of a known type, such as that manufactured by National Semiconductor, Inc. and designated as ADC808. For multiple channels, it is possible that more than one multiple input analog-to-digital converter will be used as the converter 40. For example, if an 8-input analog-to-digital converter is used and there are 24 input and output channels from the low pass filter 36, then the analog-to-digital converter 40 might include three 8-input converters.

The analog-to-digital converter 40 converts the analog signal in each input channel to a digital signal which is provided on a separate output channel to the multiple inputs of a central processing unit 42. The central processing unit is a component of a central control unit indicated generally at 44 which includes RAM and ROM memories 46 and 48. Digital input data from the analog-to-digital converter 40 is stored in memory and is processed by the CPU in accordance with a stored program to perform the diagnostic and scanning methods of the present invention. The information derived by the CPU as a result of this processing is then fed to a suitable indicator device 50 which may constitute a printer, a CRT display device, or a combination of such conventional indicators.

The operation of the discriminant analysis device 10 will be cl early understood from a brief consideration of the broad method steps of the invention which the device is intended to perform. When the lesion 14 has not been identified and a screening operation is performed to determine whether or not a lesion is present, a screening electrode array 22 is positioned in place with the central electrode 24 in the center of the site being screened and the peripheral electrodes 26 over various diverse areas of the site. If a breast 16 is screened, the electrode array may cover either the complete breast or a substantial area thereof. The reference electrode 30 is then brought into contact with the skin of the subject 12 in spaced relationship to the electrode array 22, and this reference electrode might, for example, be brought into contact with a hand of the subject. Then, the electromagnetic field between the reference electrode and each of the electrodes 24 and 26 is measured, filtered, converted to a digital signal and stored for processing by the central processing unit 42. The program control for the central processing unit causes a plurality of these measurements to be taken over a period of time, and the measurements on all channels may be taken simultaneously and repetitively for the predetermined measurement time period. Alternatively, sequential measurements between the reference electrode and one of the electrodes 24 and 26 can be taken until each channel is sampled, and then the sequential measurement is repeated for the predetermined measurement period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the central processing unit 42 at the end of the measurement period. For the duration of a single predetermined measurement period, with five measurement channels as shown, the central processor will obtain five average signals indicative of the average electromagnetic field for the period between the reference electrode 30 and each of the electrodes in the electrode array 22.

Having once obtained an average signal level indication as measured by each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of more serious disease, while a different subset might be obtained which will be indicative of the absence of serious disease. Although a number of methods and decision making logic may be designed to obtain and analyze the relationships between the average potential values in accordance with this invention for screening or diagnostic purposes, the discriminant mathmatical analysis procedure to be hereinafter described is a method which appears to be effective.

The most important relationship which may be obtained is designated the maximum voltage differential (MVD), which is defined as the minimum average voltage value obtained during the measurement period subtracted from the maximum average voltage value obtained for the same period where two or more electrodes are recording voltages from a lesion. Thus, for each predetermined measurement period, the lowest average voltage level indication obtained on a ny of the channels is subtracted from the highest average voltage level indication obtained on any one of the channels to obtain an MVD voltage level. If this MVD voltage level is above a desired level $<x$, for example, 20.0 mV, then a disease condition, such as a maligancy, may be indicated. Similarly, if the average taken over the measurement period from one channel is an abnormally low value $<y$, for example below 5.0 mV, then a disease condition, such as malignancy may also be indicated. Thus, in accordance with the present method, an abnormally low individual electrode reading (IER) or an abnormally high MVD are used to provide an indication of the existence of a disease condition. These primary indicators may be further analyzed in accordance with a control program to be subsequently described to reduce the number of false positive diagnoses, usually cases of non-malignant hyperplasia which may be falsely identified as cancer on the basis of high MVD or low IER readings.

When the device 10 is used in accordance with the method of the present invention for a screening function where a specific lesion 14 has not yet been identified, using as an example breast screening where the patient is asymptomatic, an array 22 is employed which will give maximum coverage of the entire breast surface. Then MVD levels and IER levels are obtained in accordance with the method previously described.

Figure 3:
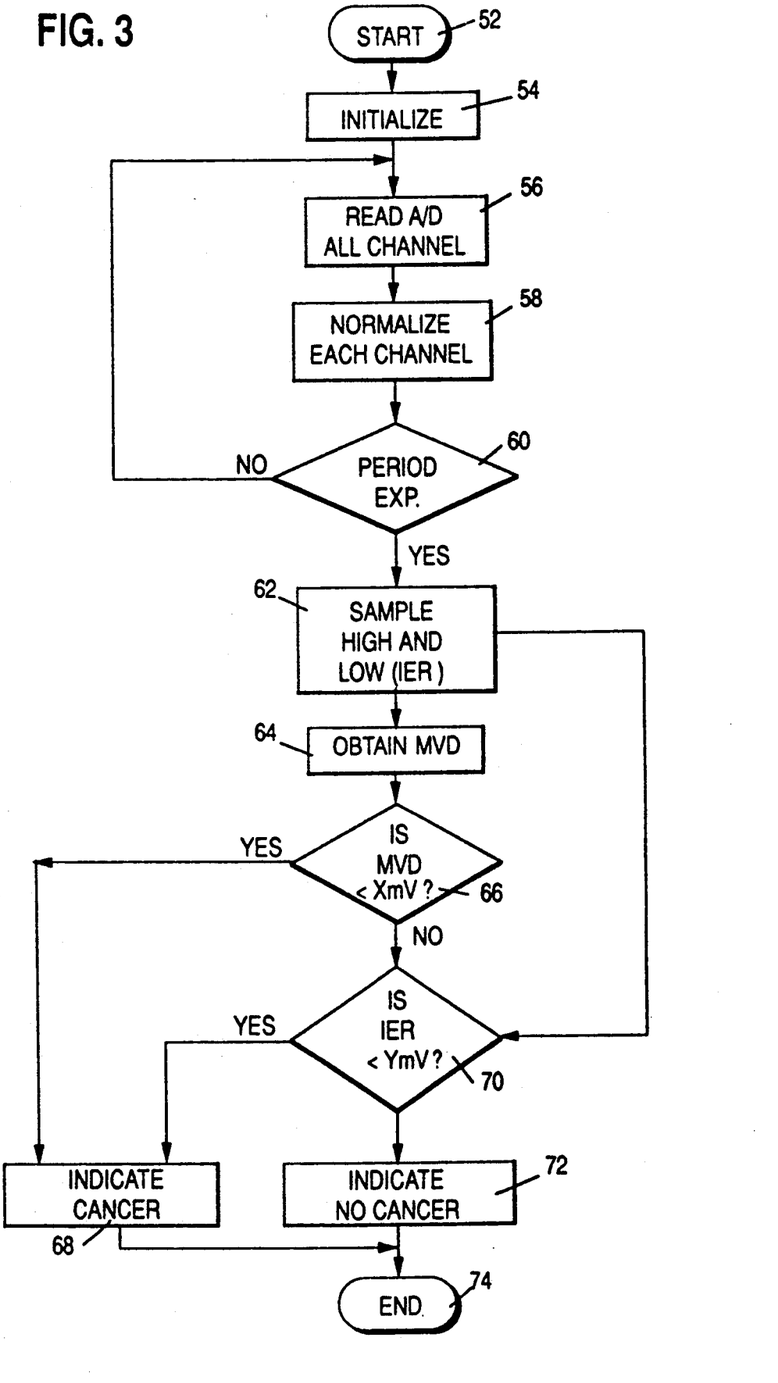
FIG. 3 is a flow diagram of the measurement operation of the apparatus of FIG. 1 used to obtain a maximum voltage differential and a low individual channel value.

The general overall operation of the central processor unit 42 will best be understood with reference to the flow diagram of FIG. 3. The operation of the unit 10 is started by a suitable start switch as indicated at 52 to energize the central processing unit 42, and this triggers an initiate state 54. In the initiate state, the various components of the device 10 are automatically brought to an operating mode, with for example, the indicator 50 of FIG. 1 being activated while various control registers for the central processing unit are reset to a desired state. Subsequently, at 56, a predetermined multiple measurement period is initiated and the digital outputs from the analog-to-digital converter 40 are read. The central processing unit may be programmed to simultaneously read all channel outputs from the analog-to-digital converter, or these channel outputs may be sequentially read.

Once all channels from the analog-to-digital converter are read, an average signal for each channel is obtained at 58 for that portion of the measurement period which has expired. The average or normalized value for each channel is obtained by summing the values obtained for that channel during the measurement period and dividing the sum by the number of measurements taken. Then, at 60, the central processor unit determines whether the measurement period has expired and the desired number of measurements have been taken, and if not, the collection of measurement samples or values continues.

Once the measurement period has expired, the microprocessor will have obtained a final average value for each channel derived from the measurements taken during the span of the measurement period. From these average values, the highest and lowest average values obtained during the measurement period are sampled at 62, and at 64, and the lowest average channel value which was sampled at 62 is subtracted from the highest sampled channel value to obtain a maximum voltage differential value.

The maximum voltage differential value is analyzed at 66 to determine if the value is greater than a predetermined level x(mV). If the maximum voltage differential is above the predetermined level, the existence of a disease condition is indicated at 68, but if it is not, then the lowest average channel output IER from 62 is analyzed at 70 to determine if this value is lower than a predetermined value (mV). If it is determined at 70 that the IER value is not lower than the predetermined value, then no disease condition is indicated at 72. On the other hand, if the IER value is lower than the predetermined value, then the presence of a disease condition is indicated at 68. After the indication of the presence or nonpresence of disease at 68 or 72, the routine is ended at 74.

Operation of the device 10 in accordance with the flow diagram of FIG. 3 for screening, provides a good indication of whether or not a disease condition is present in the area screened, and this simplified mode of operation may be used effectively for general screening purposes.

When a lesion 14 has been identified and located by screening in accordance with this invention or by other methods, a diagnosis is required to determine whether or not the lesion is malignant. For diagnostic purposes, the electrode array 22 is positioned in place with the central electrode 24 over the lesion core 18 and the peripheral electrodes 26 over various diverse areas of the outer zone 20 as well as over relatively normal tissue beyond but near the outer zone. The reference electrode 30 is then brought into contact with the skin of the subject 12 in spaced relationship to the electrode array 22, and again, for a breast malignancy diagnosis, this reference electrode might, for example, be brought into contact with a hand of the subject 12. Then, the electromagnetic field between the reference electrode and each of the electrodes 24 and 26 is measured, filtered, converted to a digital signal and stored for processing by the central processing unit 42. The central processing unit processes these signals in the same manner as previously described in connection with FIG. 3, but the operation exemplified by the flow diagram of FIG. 3 has no provision for the reduction of the number of false positive diagnoses which may be obtained from such conditions as nonmalignant hyperplasia and which can be falsely identified as cancer on the basis of high MVD levels or low IER levels. To reduce the occurrence of these false positives, the expanded flow diagram of FIGS. 4 and 5 is employed for diagnostic purposes where greater accuracy is required.

Figure 4:
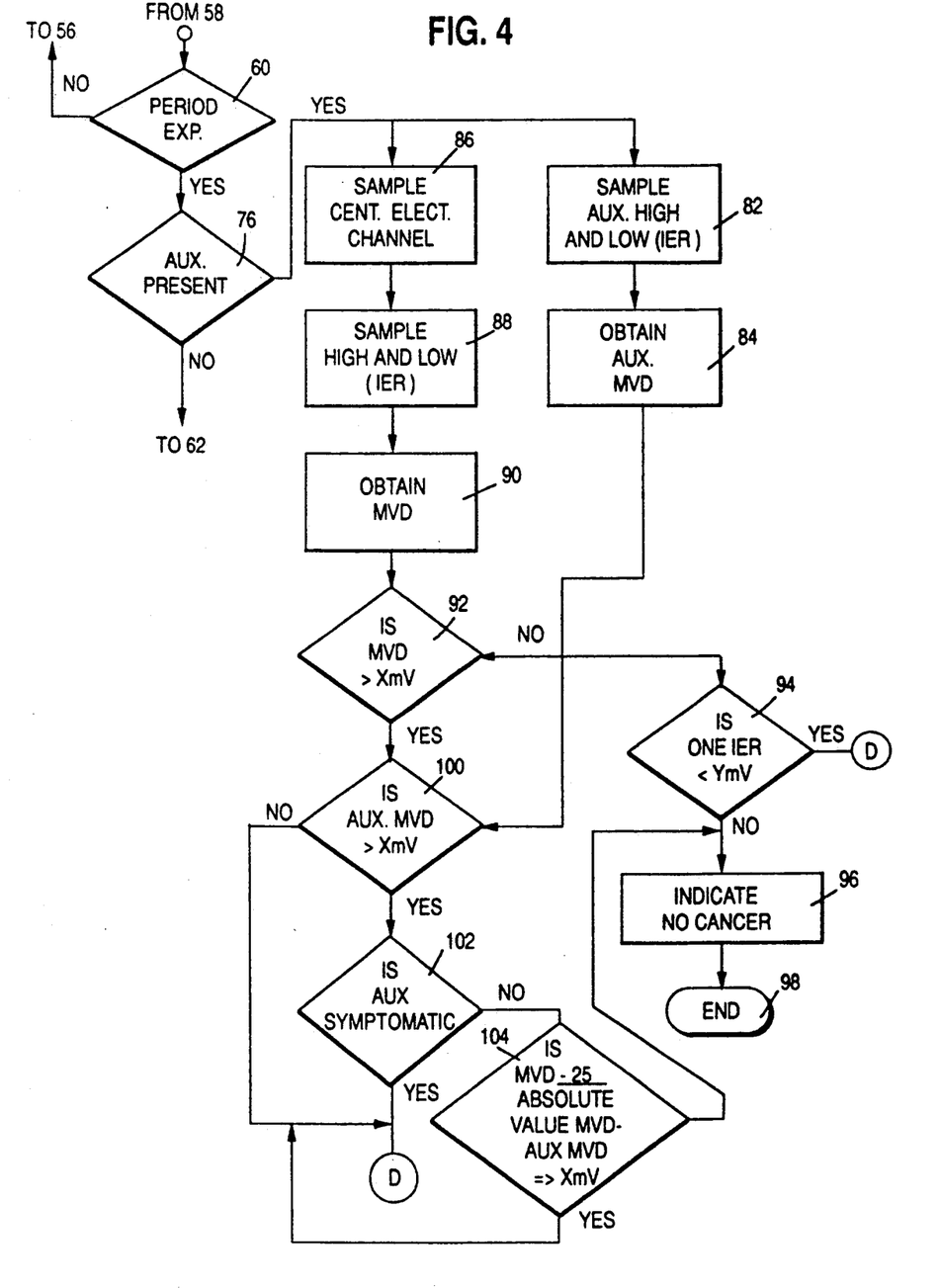
FIG. 4 is a flow diagram of the disease decision analysis provided by the apparatus of FIG. 1.
Figure 5:
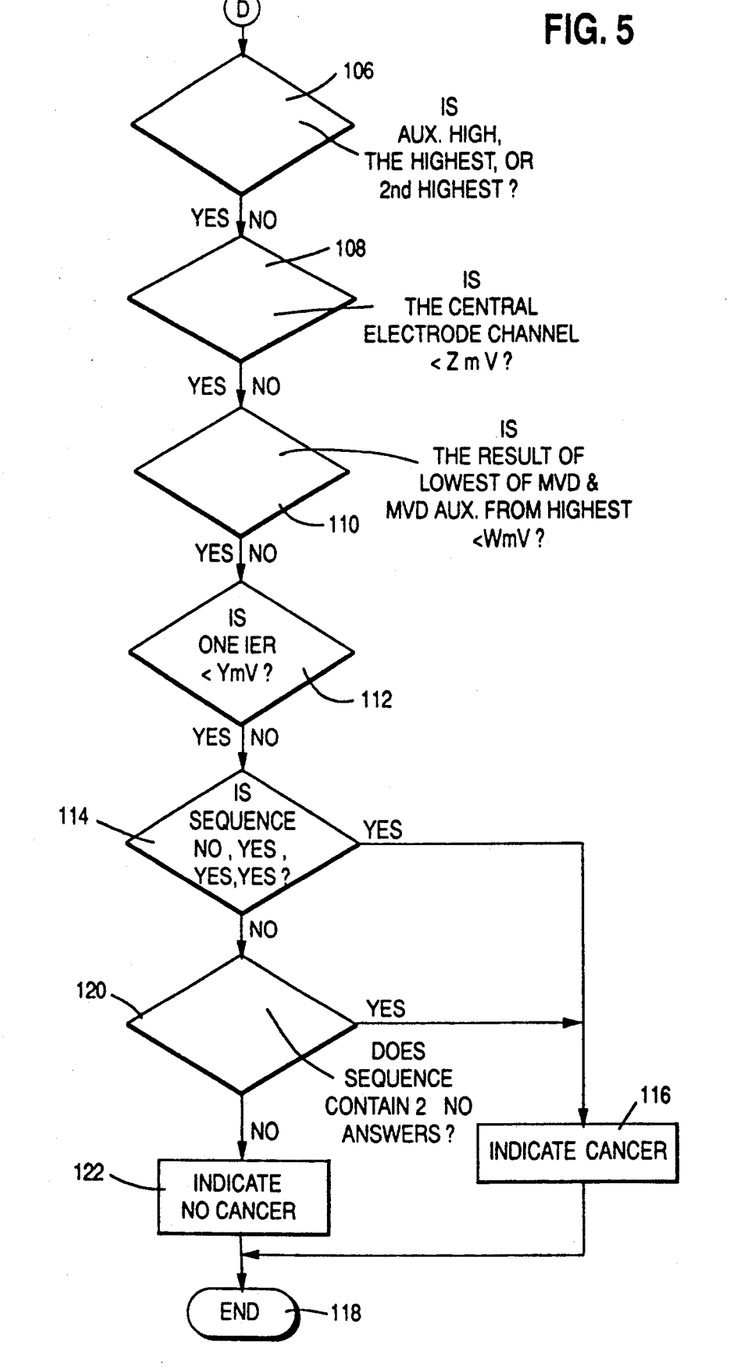
FIG. 5 is a flow diagram of an auxilliary decision sequence used with the flow diagram of FIG. 4.

Referring now to FIG. 4, the initial portion of the flow diagram of FIG. 3 down to the determination of the expiration of the measurement period at 60 is incorporated by reference. Once the measurement period expires, the system operates at 76 to determine if auxiliary measurements are present. If such auxiliary measurements are not present, then the flow diagram passes on to the sampling process 62 of the flow diagram of FIG. 3 and continues on through this flow diagram which is incorporated by reference.

On the other hand, if auxiliary measurements are sensed, then the flow diagram of FIG. 4 proceeds with an analysis of the primary measurement channels as well as the auxiliary measurement channels. To understand the source of the auxiliary measurements, it can be noted from FIG. 1 that multiple measurements can be taken and averaged from a symptomatic organ, such as the breast 16 and also from a similar asymptomatic or symptomatic organ such as the opposite breast 78. The measurements obtained from the breast 78 and from the core electrode 24 can form the auxiliary channel measurements, while those obtained from the breast 16 form the primary channel measurements. The auxiliary channel measurements may be taken sequentially after the primary channel measurements, or alternatively, may be taken simultaneously by using a second electrode array 80. The primary and secondary channels would be separated as they pass through the low pass filter 36 and analog-to-digital converter 40 to the central processing unit 42, but otherwise the measurements and averaging would occur for the auxiliary channels in exactly the same manner as previously described in connection with the primary channels.

Returning to FIG. 4, if the presence of auxiliary channels are sensed at 76, then the high and low auxiliary channel values are determined at 82, and a maximum voltage differential for the auxiliary channel high and low values is determined at 84. At the same time, the average value for the channel dedicated to the central electrode 24 is determined at 86 and the high and low average channel values for the primary measurement channels are determined at 88. Then at 90, the maximum voltage differential for the primary measurement channels is determined and at 92 a decision is made as to whether or not the primary measurement channel maximum voltage differential exceeds a predetermined voltage x.

As in the case of the flow diagram of FIG. 3, if the predetermined voltage x is not exceeded by the primary channel maximum voltage differential at 92, then at 94 a determination is made as to whether there is at least one low average value for the primary measurement channels which is less than a predetermined voltage level v. If there is, then the decision making logic of FIG. 5 comes into operation, but if there is not, then a NO CANCER indication is provided at 96 and the routine ends at 98.

Should the determination at 92 show that the primary channel maximum voltage differential is greater than the predetermined value x, then at 100, a determination is made as to whether or not the auxiliary channel maximum voltage differential is greater than x. If the auxiliary channel maximum voltage differential is less than x, then the decision sequence of FIG. 5 is instituted. On the other hand, if this auxiliary maximum voltage differential is greater than x, then a decision is made at 102 as to whether or not the second breast 78 is symptomatic or asymptomatic. If this breast is symptomatic, then the decision logic flow diagram of FIG. 5 is instituted, but if the breast is not symptomatic, then an equation at 104 is performed. Basically, the equation at 104 determines whether the primary channel maximum voltage differential minus 25 divided by the absolute value of the primary channel maximum voltage differential minus the auxiliary channel multiple voltage differential is equal to a value greater than the predetermined value x. If it is, then the decision sequence flow diagram of FIG. 5 is instituted, but if it is not, then a NO CANCER indication is provided at 96 and the routine is terminated at 98.

Turning now to FIG. 5, the decision sequence flow diagram involves initially answering a sequence of four questions indicated at 106, 108, 110 and 112. These questions are answered using the data obtained from the operation in accordance with the flow diagram of FIG. 4. At 106, a determination is made as to whether or not the highest average value obtained from the auxiliary channel is the highest or second highest value obtained from all channels. Then, at 108, a determination is made as to whether or not the central electrode channel value is less than a predetermined value z. After this determination, a determination is made at 110 as to whether or not the disparity between the maximum voltage differential from the primary channel and the maximum voltage differential from the auxiliary channel is less than a predetermined value w.

The final sequential question is a determination as to whether at least one average value for a channel (IER) is less than y. Once this sequence of questions has been answered, then at 114 a determination is made as to whether the sequence of answers is "no", "yes", "yes", "yes". If this sequence of answers is present, then CANCER is indicated at 116 and the routine is ended at 118.

Conversely, if the proper sequence of answers is not found at 114, then at 120 it is determined whether or not the sequence of answers contains two "no" answers. If it does, then CANCER is indicated at 116 and the routine is terminated at 118, but if it does not, then an indication of NO CANCER is provided at 122 and the routine is terminated at 118.

The control program represented by the flow diagrams of FIGS. 3-5 can be altered to preset values of w, x, y and z which are found to be most effective for a diagnosed condition. For breast cancer diagnosis, the following values have been effectively used:
w 10 mV
x 20 mV
y 5 mV
z 42 mV The device 10 and method of the present invention operating in accordance with the flow diagrams of FIGS. 4 and 5 have been tested on 102 women with suspicious breast lesions. A correct diagnosis of CANCER was obtained in all 39 cases where cancer was verified by biopsy (there were no false negatives). It is also noteworthy that the percentage of false positives was less than 14%, a result which exceeds that of the more traditional methods of attempting to identify cancer on the basis of electronegative polarity.

Figure 6:
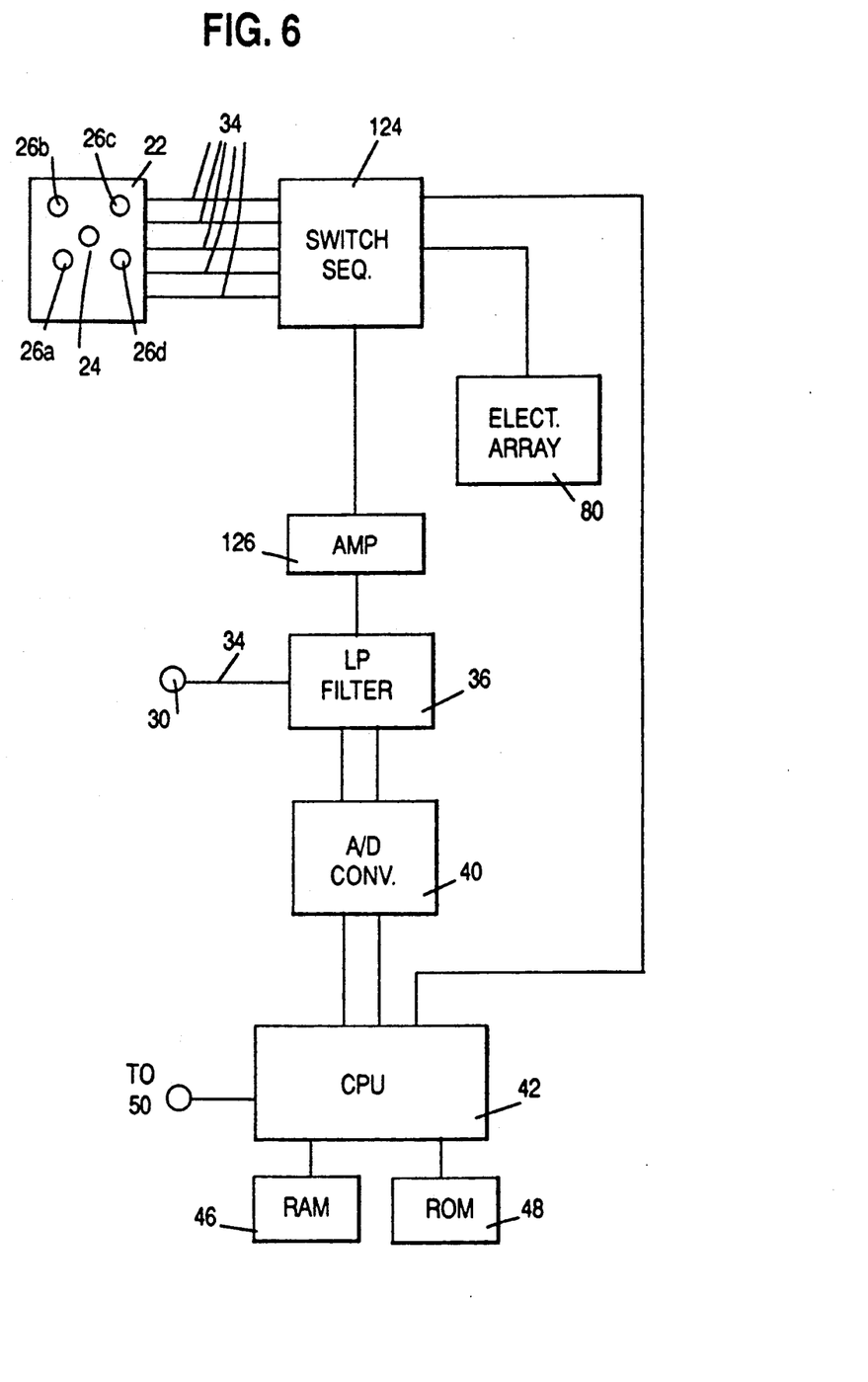
FIG. 6 is a block diagram of a second embodiment of the apparatus of the present invention.

The discriminant analysis device of the present invention may be constructed to sequentially sample the output from each electrode 26 and provide sampled potentials over a single one amplifier channel. A sequential system of this type is shown in FIG. 6 where the outputs from the electrodes 24 and 26 are fed to a switching sequencer 124 which operates under the control of the central processor 42. The central processor causes the switching sequencer to sequentially provide the outputs from specific electrodes in sequence to an amplifier 126 and the low pass filter 36. Thus, a single amplifier and a single channel to the filter 36 handle all of the outputs from the electrode array 22, and also the outputs from electrode array 80 when this array is used.

When the switching sequencer 124 is provided under the control of the central processor 42, the reference electrode 30 may well be eliminated and an electrode in either the electrode array 80 or the electrode array 22 may function as the reference electrode. This is often advantageous, as it will place the reference electrode closer to the disease site and will substantially reduce or eliminate the effects of long term drift which occur when the reference electrode is remote from the disease site. Also, this provides great flexibility in measurement technique. For example, a single electrode in either the array 80 or the array 22 can be chosen as the reference electrode for all measurements taken during a measurement period. On the other hand, the sequencer could choose different reference electrodes during the measurement period to provide measurements from different test and reference electrode combinations. In a sequential measurement operation, the sequencer could choose the electrode 26a of FIG. 6 as a reference electrode for taking a measurement with the electrode 26b as the test electrode, and then the electrode 26b could be sequenced to become the reference electrode while a measurement is taken with the electrode 26c. This sequence can continue using all electrodes or selected electrodes in the matrix during the test period. The electrodes in both the arrays 22 and 80 can be sequenced to obtain measurements from a variety of reference and test electrode combinations.

Industrial Applicability

The method and apparatus of the present invention may be employed to effectively screen or diagnose disease states by using skin surface potentials taken from a number of different areas on a known or suspected disease site. Malignancy can be indicated with great accuracy while the incidence of false positive diagnosis due to such effects as cases of nonmalignant hyperplasia are minimized.

What is claimed is:
1. An apparatus for disease screening or diagnosis at a potential disease site on a human or animal subject by measuring the electrical potentials which are a function of the electromagnetic fields which originate from within the subject and are present on the skin surface of the subject in an area of said potential disease site, comprising
a plurality of electrode means adapted for contact with the skin surface of the subject at spaced locations in the area of the potential disease site to detect only the potentials of said electromagnetic fields which originate from within the subject and are present in the area of said potential disease site during a test period and to provide test potentials as a function of each of said potentials detected, and processing means connected to receive said test potentials provided by said electrode means, said processing means operating during said test period to select at least one of said electrode means as a reference electrode and another of said electrode means as a test electrode and to cause said test electrode to operate with said reference electrode to detect the potential of the electromagnetic field present therebetween and to provide a test potential as a function thereof.

2. The apparatus for disease screening or diagnosis of claim 1, wherein said processing means operates to select from said electrode means a plurality of different test electrode-reference electrode combinations during the test period and to receive test potentials from each of said plurality of combinations.

3. The apparatus for disease screening or diagnosis of claim 2, wherein said processing means operates to sample and receive a plurality of test potentials from each of said selected test electrode-reference electrode combinations during the test period and to average the test potentials for each of said test electrode-reference electrode combinations to obtain an average signal therefor at the end of the test period, said processing means operating to compare said average signals obtained for a test period to identify potential difference relationships therebetween.

4. The apparatus for disease screening or diagnosis of claim 3, wherein said electrode means include a plurality of spaced electrodes mounted in a unitary electrode matrix.

5. The apparatus for disease screening or diagnosis of claim 2 wherein said processing means includes sequencer switching means connected to said electrode means and operative to select said plurality of test electrode-reference electrode combinations and to receive the test potential from the plurality of selected test electrode-reference electrode combinations.

6. The apparatus for disease screening or diagnosis of claim 5 wherein said processing means includes amplifier means connected to said sequencer switching means to receive and amplify test potentials from said sequencer switching means.

7. The apparatus for disease screening or diagnosis of claim 6 wherein said amplifier means includes a single amplifier for receiving all test potentials from said sequencer switching means.

8. The apparatus for disease screening or diagnosis of claim 7 wherein said processing means includes analog-to-digital converter means connected to separately receive each said test potential from said amplifier means for providing a separate digital test signal indicative of each said test potential obtained during said test period.

9. The apparatus for disease screening or diagnosis of claim 8 wherein said processing means includes filter means between said amplifier and said analog to digital converter means, said filter means including a single low pass filter, said filter means and amplifier means forming a single channel between said sequencer switching means and said analog-to-digital converter means for said test potentials.

10. The apparatus for disease screening or diagnosis of claim 5 wherein said processing means includes analog-to-digital converter means connected to separately receive each said test potential from said sequencer switching means for providing a separate digital test signal indicative of each said test potential obtained during said test period, and central processor means connected to separately receive each said separate digital test signal, said processor means operating to compare said digital test signals obtained during said test period to identify potential relationships therebetween indicative of the presence of a disease condition.

11. The apparatus for disease screening or diagnosis of claim 10 wherein said central processing means comprises digital test signal comparing said digital test signals to obtain a maximum voltage differential by obtaining from the digital test signals for said measurement period maximum and minimum digital signals and subsequently obtaining a differential value signal indicative of the difference between said maximum and minimum digital signals.

12. The apparatus for disease screening or diagnosis of claim 11, wherein said central processor means further comprises differential value signal comparing means for comparing said differential value signal to a first reference value, and providing an output signal indicative of the presence of a disease condition in accordance with a relationship between said first reference value and said differential value signal.

13. An apparatus for disease screening or diagnosis at a potential disease site on a human or animal subject by measuring the electrical potentials which are a function of the electromagnetic field present on the skin surface of the subject in an area of said potential disease site comprising a plurality of electrode means adapted for contact with the skin surface of the subject at spaced locations in the area of the potential disease site to detect the potentials of electromagnetic fields present in the area of said potential disease site during a test period and to provide test potentials as a function of each of said potentials detected;

processing means connected to receive said test potentials from said electrode means, said processing means operating during said test period to select at least one of said electrode means as a reference electrode and another of said electrode means as a test electrode and to cause said test electrode to operate with said reference electrode to detect the potential of the electromagnetic field present therebetween and to provide a test potential as a function thereof, wherein said processing means further operates to select from said electrode means a plurality of different test electrode-reference electrode combinations during the test period and to receive test potentials from each of said combinations; and wherein said processing means includes sequencer switching means connected to said electrode means and operative to select said test electrode means and operative to select said test electrode-reference electrode combinations and to receive the test potential from said selected test electrode-reference electrode combinations;

analog-to-digital converter means connected to separately receive each said test potential from said sequencer switching means for providing a separate digital test signal indicative of each said test potential obtained during said test period;

and central processor means connected to separately receive each said separate digital test signal, said processor means operating to compare said digital test signals obtained during said test period to identify potential relationships therebetween indicative of the presence of a disease condition; and wherein said central processor means further comprises digital test signal comparing means for comparing said digital test signals to obtain a maximum voltage differential by obtaining from the digital test signals for said measurement period maximum and minimum digital signals and subsequently obtaining a differential value signal indicative of the difference between said maximum and minimum digital signals, differential value signal comparing means for comparing said differential value signal to a first reference value, and providing an output signal indicative of the presence of a disease condition in accordance with a relationship between said first reference value and said differential value signal, and minimum digital signal comparing means that operates when the relationship between said first reference value and said differential value signal is not indicative of the presence of a disease condition for comparing said minimum digital signal to a second reference value, and providing an output signal indicative of the presence of said disease condition in accordance with a second relationship between said second reference value and said minimum digital signal.

14. The apparatus for disease screening or diagnosis of clam 13, wherein said central processor means further comprises output signal means for providing an output signal indicative of the presence of said disease condition if said differential value signal is of a greater value than said first reference value and if said minimum digital signal is of a lesser value than said second reference value.

15. A method for determining the presence or absence of a disease condition at a test site on a human or animal subject as a function of the potential of an electromagnetic field which originates from and is present in the subject sensed by a plurality of spaced electrodes in contact with the skin surface of the subject in the area of the test site, which includes:
sequentially selecting during a test period pairs of electrodes from said plurality of spaced electrodes and detecting only the respective electrical potential of the electromagnetic filed which originates from and is present in the subject between each of said selected pairs of electrodes,
comparing the respective electrical potentials so obtained to identify a high and a low level potential,
obtaining a differential value indicative of the difference between said high and low level potentials,
comparing said differential value to a predetermined reference value to determine a relationship therebetween, and
obtaining an indication of the presence or absence of a disease condition from said relationship of the differential value to the reference value.

16. The method of claim 15 which includes selecting in sequence different single pairs of said electrodes during the test period to obtain electrical potentials from a plurality of different electrode pairs.

17. The method of claim 16 which includes taking a plurality of electrical potential measurements from each said selected electrode pair during the test period,
obtaining an average measurement value from the potential measurements taken by each selected electrode pair during the test period,
an comparing said average measurement values to identify therefrom said high and low level potentials.

18. A method for determining the presence or absence of a disease condition at a test site on a human or animal subject as a function of the potential of the electromagnetic field present in the subject sensed by a plurality of spaced electrodes in contact with the skin surface of the subject in the area of the test site which includes:
sequentially selecting during a test period different pairs of electrodes from said plurality of spaced electrodes and detecting the respective electrical potential of the electromagnetic field in the subject between each selected pair of electrodes to obtain electrical potentials from a plurality of different electrode pairs,
comparing the individual respective electrical potentials so obtained to identify a high and a low level potential,
obtaining a differential value indicative of the difference between said high and low level potentials,
comparing said differential value to a predetermined reference value to determine a relationship therebetween,
taking a plurality of electrical potential measurements from each said selected electrode pair during the test period,
obtaining an average measurement value from the potential measurements taken by each selected electrode pair during the test period,
comparing said average measurement values to identify therefrom said high and low level potentials, and
obtaining an indication of the presence or absence of a disease condition based upon whether said differential value exceeds or is less than said predetermine reference value,
if the absence of a disease indication is indicated, comparing said low level potential to a second predetermine reference value to determine a second relationship therebetween,
and obtaining a second indication of the presence or absence of said disease condition from the second relationship of said low level potential to said second reference value.

* * * * *